US005851836A

United States Patent [19]
Enomoto

[11] Patent Number: 5,851,836
[45] Date of Patent: Dec. 22, 1998

[54] METHOD FOR DETERMINING FIBRINOGEN AND REAGENT FOR DETERMINATION THEREOF

[75] Inventor: Masayasu Enomoto, Takatsuki, Japan

[73] Assignee: Nippon Shoji Kaisha Ltd., Osaka, Japan

[21] Appl. No.: 521,868

[22] Filed: Aug. 31, 1995

[30] Foreign Application Priority Data

Sep. 2, 1994 [JP] Japan .................................. 6-209940

[51] Int. Cl.$^6$ .................................................. G01N 33/49
[52] U.S. Cl. ............................... 436/69; 436/74; 435/13
[58] Field of Search ................................... 436/8, 16, 18, 436/69, 74, 79, 87, 34, 63; 422/73; 435/2, 13

[56] References Cited

U.S. PATENT DOCUMENTS

| | | | |
|---|---|---|---|
| 4,692,406 | 9/1987 | Becker et al. | 435/13 |
| 5,223,437 | 6/1993 | Hoffman et al. | 436/164 |
| 5,292,664 | 3/1994 | Fickenscher | 436/69 |
| 5,508,202 | 4/1996 | Enomoto et al. | 436/69 |

FOREIGN PATENT DOCUMENTS

| | | |
|---|---|---|
| 2096215 | 11/1993 | Canada . |
| 570354 | 11/1993 | European Pat. Off. . |
| 632270 | 1/1995 | European Pat. Off. . |
| 54-023596 | 2/1979 | Japan . |
| 60-053848 | 3/1985 | Japan . |
| 60-058555 | 4/1985 | Japan . |
| 63-305255 | 12/1988 | Japan . |
| 5-060764 | 12/1993 | Japan . |

OTHER PUBLICATIONS

De Cristofaro et al., *Modulation of Thrombin–Fibrinogen Interaction by Specific Ion Effects*, Biochemistry, vol. 31, No. 1, 1992, pp. 257–265.
Belitser et al., *Ukr. Biokhim. Zh.*, 5, 567–579 (1975).
Blombäck et al., *Thrombosis Research*, 25, 51–70 (1982).

*Primary Examiner*—Lyle A. Alexander
*Attorney, Agent, or Firm*—Leydig, Voit & Mayer, Ltd.

[57] ABSTRACT

A method for determining fibrinogen concentration whereby thrombin or a protease inhibitor having similar activity thereto is added to an undiluted to test sample to convert fibrinogen in the sample to fibrin, and determining a coagulation time fibrinogen is converted in a reaction mixture containing a salt at a high concentration and a reagent therefor. The determination in the presence of a salt at a high concentration permits simplified determination without diluting the test sample.

24 Claims, 9 Drawing Sheets

FIG. 1

Concentration of salt added

METHOD FOR DETERMINING FIBRINOGEN AND REAGENT FOR DETERMINATION THEREOF

FIELD OF THE INVENTION

The present invention relates to a method for determining fibrinogen without diluting a plasma sample and to a reagent therefor.

BACKGROUND OF THE INVENTION

Fibrinogen is a glycoprotein having a molecular weight of 340,000, and is an important blood coagulation factor involved in the final reaction of blood coagulation. Fibrinogen undergoes limitative degradation into fibrin by the action of thrombin, forms aggregates and leads the coagulation reaction to the completion, for which mechanism it is indispensable to the coagulation reaction. Variation in the level of fibrinogen in the blood is closely related to various diseases. The fibrinogen level becomes higher in various infectious diseases, malignant tumor, cerebral apoplexy, myocardial infarction, collagen disease, diabetes, gestosis, nephrosis and the like, and decreases in congenital fibrinogenopenia, hepatopathy, massive bleeding, diffuse intravascular coagulation (DIC) and promoted fibrinolysis.

As described, the determination of fibrinogen level is one of the important blood coagulation tests for the diagnoses of various diseases and haematological diagnoses.

There have been known many methods for determining fibrinogen. Generally divided, there are a coagulative determination method comprising determining the process of, or a product generated by, the formation of fibrin from fibrinogen by thrombin, a method comprising immunoassay of fibrinogen itself, and a turbidity method using salting out (Japanese Patent Unexamined Publication No. 53848/1985).

The immunoassay and turbidity method cannot sufficiently identify abnormal fibrinogen, and fibrinogen, fibrin and its degraded products, nor can they remove non-specific reactions, which in turn results in unprecise determination of fibrinogen, complicated determination operations and extended assay time (for example, the assay time in Japanese Patent Unexamined Publication No. 53848/1985 was not less than 30 minutes).

One of the blood coagulative determinations comprises determination of fibrinogen level based on the optical and time data calculated in the course of measuring prothrombin time, partial thromboplastin time or activated partial thromboplastin time (Japanese Patent Unexamined Publication Nos. 58555/1985, 305255/1988, 60764/1993). These methods comprise not only measuring optical density and varying optical dispersion, but also calculating fibrinogen level from the optical and measurement-time data. Such method imposes great economical burden caused by the use of an optical system inclusive of calculation apparatuses. In addition, the determination values lack precision.

The method most commonly used in routine tests as a blood coagulative determination is the Thrombin Time Method. This method comprises adding a sufficient amount of thrombin to a diluted plasma to allow thrombin to convert fibrinogen to fibrin, and measuring the coagulation time up to the occurrence of fibrin coagulation, based on which the fibrinogen concentration is determined. The coagulation time is dependent upon the fibrinogen concentration in the test sample, and an increase in fibrinogen concentration results in a shorter coagulation time. In the Thrombin Time Method, instantaneous (within 4 seconds) coagulation takes place in a plasma containing fibrinogen in a normal proportion (ca. 200–400 mg/dl), so that the plasma needs to be diluted to the level which allows determination. Generally, the plasma is diluted 10-fold. When the concentration of fibrinogen in plasma is extremely high or low, re-dilution is done before determination.

This method is associated with a problem caused by very complicated manipulation for the determination, since a diluting step is necessary. In addition, a diluted plasma produces only very fragile and small clots, which results in inferior determination precision in comparison with other coagulation tests such as those according to the prothrombin time method using an undiluted plasma. Clots are generally determined using a determination device. Hence, the fibrinogen determination using a diluted plasma is not essentially suitable for the determination using a device, since only trace amounts of clots are produced in the diluted plasma.

For solving such problems, there have been proposed optical determinations (Japanese Patent Unexamined Publication Nos. 23596/1979, 503008/1993 corresponding to U.S. Pat. No. 5,223,437, 66996/1985 corresponding to U.S. Pat. No. 4692406). These methods lack generality and their applicable range is extremely limited. The method of Japanese Patent Unexamined Publication No. 503008/1993 requires complicated manipulations necessary for using diluted plasma; the method of Japanese Patent Unexamined Publication No. 23596/1979 requires a plasma sample as a control in absorbance measurement; and the method of Japanese Patent Unexamined Publication No. 66996/1985 is complicated as a method for fibrinogen determination, since fibrinogen and fibrinogen degradation product are simultaneously determined in this method.

For the purpose of solving the problems of these conventional methods, there has been proposed a fibrinogen determination method comprising measuring the coagulation time using an undiluted plasma (Japanese Patent Unexamined Publication Nos. 219993/1993 corresponding to U.S. Pat. No. 5,292,664, 46898/1994 corresponding to EP-A-570354).

In Japanese Patent Unexamined Publication No. 219993/1993, fibrin coagulation is partially suppressed to delay the coagulation time by the use of a specific peptide which is a fibrin coagulation inhibitor, whereby a test sample containing fibrinogen at a high concentration, namely, an undiluted plasma can be determined. The fibrin coagulation inhibitor to be used is known, and GLY-PRO-ARG-PRO is described in a catalog of Sigma, USA. Such peptide is very expensive (GLY-PRO-ARG-PRO 1 mg costs 11.25 U.S. dollars), and the economical burden becomes great in view of the concentration at which the inhibitor is used. In addition, this method generally requires long time for coagulation, and the coagulation time and fibrinogen concentration are not in a linear relationship on a log-log graph. (Note that a linear relationship is generally found in the Thrombin Time Method). The lower determination limit of fibrinogen is considered to be 0.6 g/L. When an undiluted plasma is used, the lower determination limit is the lower, the better.

The method of Japanese Patent Unexamined Publication No. 46898/1994 is characterized by the determination at an acidic pH range of from 4 to 7.3. In this Publication, the determination is conducted in a buffer having a molar concentration of the buffer salt of 0.02–0.5M, which has been made to have a greater ionic strength by the addition of a salt such as sodium chloride to the buffer. One characteristic of this method is that it is free from the influence of thrombin inhibitors such as heparin and antithrombin III (AT III). In the Examples, the influence of heparin is compared at pH 6 and pH 8. The problem of this method is that a pH markedly distant from the optimal pH (near 8.0) of thrombin is employed as a preferable pH (acidic pH 6 was used as the most preferable pH) and the amount of the thrombin used was less (10 NIHU/ml) than the amount generally used for the fibrinogen determination. The use of a small amount of thrombin and the determination at a pH markedly distant from the optimal pH lead to a very low substantive thrombin activity. This method is problematic in terms of determination precision, since it is deviated from the basic principle of the Thrombin Time Method, which is the use of an excess amount of thrombin. When the coagulation time is plotted on a log-log graph relative to the fibrinogen concentration, a linear relationship cannot be obtained, and the method fails to provide a sufficient determination at low levels of fibrinogen.

Figure 8:
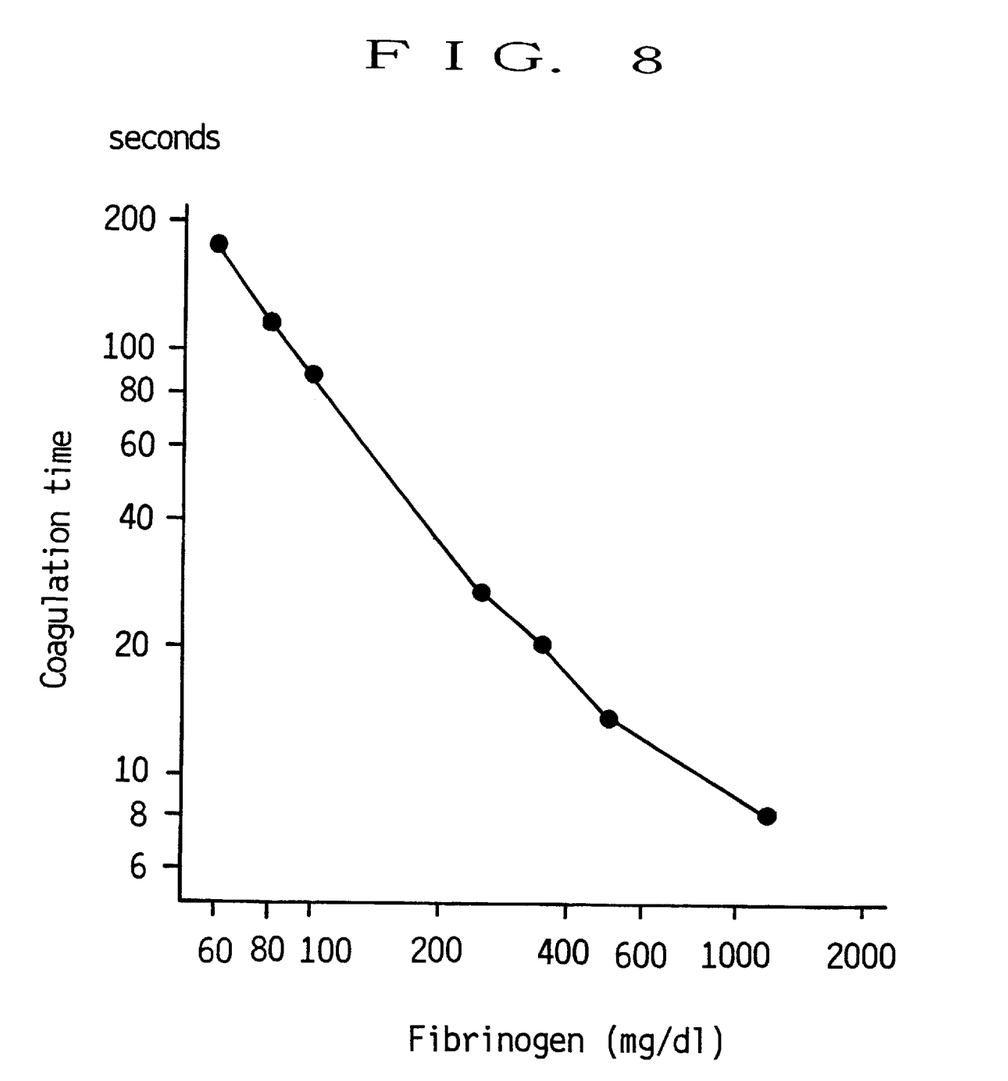
FIG. 8 is a graph showing the determination results according to the conventional method (Japanese Patent Unexamined Publication No. 219993/1993) plotted on a log-log graph.
Figure 9:
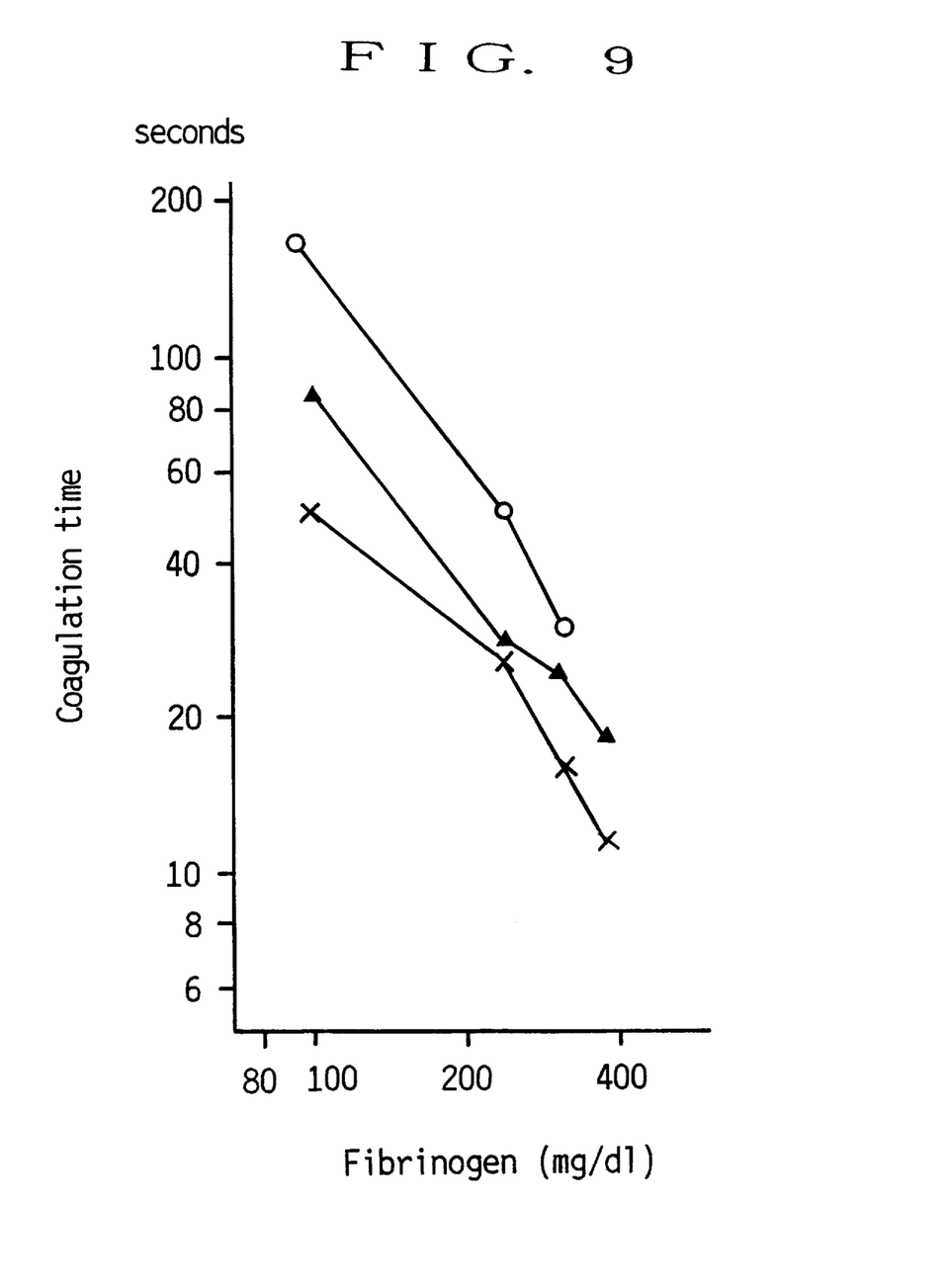
FIG. 9 is a graph showing the determination results according to the conventional method (Japanese Patent Unexamined Publication No. 46898/1994) plotted on a log-log graph. In the Figure, ○—○ is meizothrombin, pH 6; ▲—▲ is thrombin, pH 6; and x—x is thrombin, pH 8.

The determination results of Japanese Patent Unexamined Publication Nos. 219993/1993, Example 2 (A), and 46898/1994, Example in the absence of heparin, were plotted on a log-log graph and shown in FIG. 8 and FIG. 9, respectively. According to these conventional methods, coagulation time and fibrinogen concentration are not in a linear relationship.

SUMMARY OF THE INVENTION

It is therefore an object of the present invention to provide a simple and economical method permitting fibrinogen determination without diluting a plasma sample but using a coagulation time measurement equipment generally used for coagulation tests, and a reagent therefor.

According to the present invention, there is provided a method based on the Thrombin Time Method, which comprises reaction in the presence of a salt at a high concentration without diluting a test sample and which can achieve a desirable length of coagulation time.

The present invention provides a method for determining fibrinogen in a test sample, comprising adding thrombin or a protease having a similar activity thereto to a test sample to convert fibrinogen in the sample to fibrin, and determining a coagulation time, wherein an undiluted sample is used and the fibrinogen is converted in a reaction mixture containing a salt at a high concentration.

The present invention also relates to a reagent for fibrinogen determination, comprising a salt at a high concentration, and 20–500 NIHU/ml thrombin or a protease having a similar activity.

According to the method of the present invention, a sample having a low fibrinogen concentration can be assayed using a normal amount of thrombin and an undiluted plasma, by an extremely economical method of increasing the salt concentration, without using expensive peptide or excessively prolonging the coagulation time.

The method of the present invention affords a good correlation with the determination values obtained by commercially available determination reagent kits according to the conventional Thrombin Time Method using a diluted plasma.

DETAILED DESCRIPTION OF THE INVENTION

In the present invention, a salt at a high concentration means a salt at a higher concentration than the physiological concentration widely used for general blood coagulation tests. To be specific, a sample containing fibrinogen (275 mg/dl), and a reagent containing thrombin (100 NIHU/ml) and HEPES (100 mM, pH 7.35) are mixed at a volume ratio of 1:2 and adjusted to have a salt concentration which produces 5–100 seconds, preferably 7–50 seconds and more preferably 10–30 seconds of coagulation time at 37° C.

According to the method of the present invention, fibrinogen in a sample is converted to fibrin by the action of thrombin or a protease having a similar activity. The coagulation time varies depending on the fibrinogen concentration, and when the determination conditions are the same, the coagulation time corresponds to the fibrinogen concentration. Comparison thereof with the coagulation time of the standard leads to the determination of fibrinogen.

In the method of the present invention, the determination is conducted at a pH near physiological pH (pH 7.3) and at a pH within the range including the optimal pH of thrombin. Preferred pH is from 6.0 to 9.0, more preferably from 7.0 to 8.0.

The origin of the thrombin to be used in the present invention is not particularly limited, and thrombins derived from human, cow, horse, goat and the like can be used, and they are commercially available. The "similar activity" in "a protease having a similar activity" means the protease activity which forms fibrin by acting on fibrinogen. The origin of such protease is not particularly limited, and batroxobin, a protease derived from venom of a snake (academic designation: *Agkistrodon rhodostoma*) and the like can be used.

When thrombin is used in the present invention, an excess amount of at least 20 NIHU is added per 1 ml of plasma. When a protease having a similar activity is used, an amount thereof is added, which shows a similar activity when converted to thrombin. The concentration of thrombin or a protease having a similar activity in a reaction mixture is generally 10–200 NIHU/ml, preferably 20–100 NIHU/ml.

In the method of the present invention, a sample and a reagent containing thrombin or a protease having a similar activity are mixed at a volume ratio of 1:1–1:8, preferably 1:2–1:3.

As a salt to be used for the determination, a halide of alkali metal or alkaline earth metal is generally used. Examples of such salt include sodium salt, potassium salt, calcium salt and magnesium salt. Preferred are sodium chloride, sodium bromide, sodium iodide, potassium chloride, potassium bromide, potassium iodide, calcium chloride and magnesium chloride. When these preferable salts are used, the salt concentration in the reaction mixture is 0.25–3M, preferably 0.5–2.5M, more preferably 1–2M for sodium chloride; 0.1–1.0M for sodium bromide; 0.1–0.4M for sodium iodide; 0.25–1.5M for potassium chloride; 0.1–1M for potassium bromide; 0.1–0.4M for potassium iodide; 0.04–0.25M for magnesium chloride; and 0.04–0.25M for calcium chloride.

The above-mentioned salts may be used alone or in combination. When two or more kinds of salts are used, the combination thereof is not limited. Preferred combination is that of sodium chloride and other salt, more preferably that of sodium chloride and sodium bromide.

When two or more kinds of salts are used, a sample containing fibrinogen (275 mg/dl) and a reagent containing thrombin (100 NIHU/ml) and HEPES (100 mM, pH 7.3) are mixed at a volume ratio of 1:2, and adjusted to have a salt concentration which produces 5–100 seconds, preferably 7–50 seconds and more preferably 10–30 seconds of coagulation time at 37° C. For example, the salt concentration is adjusted to 1.0–2.5M of sodium chloride and 0.1–0.8M of sodium bromide.

In practice, the coagulation time is adjusted to a preferable one by appropriately selecting the kind and concentration of the salt to be used. In general, the coagulation time extends with increasing salt concentrations. When sodium chloride or potassium chloride is used, for example, the coagulation time is shortened at a concentration exceeding a certain level (see FIG. 1).

When a coagulation time measurement equipment is used, a salt concentration which makes the coagulation time 10–30 seconds is preferable for assaying a normal sample containing 275 mg/dl fibrinogen. While the coagulation time may vary depending on other substances in the reagent, such as bovine serum albumin (BSA), polyethylene glycol, surfactant and the like, it can be adjusted by appropriately selecting the kind and concentration of the salt or by combining two or more kinds of salts. Although the coagulation time may vary depending on the concentration of thrombin in the reagent, it is not desirable to prolong the coagulation time by reducing the thrombin concentration. In addition, a determination using a small amount of thrombin at a pH markedly different from the optimal pH range of thrombin, like the method described in Japanese Patent Unexamined Publication No. 46898/1994, is undesirable, since the determination is conducted under the conditions which make the thrombin activity substantially markedly low.

For a good correlation with the conventional Thrombin Time Method using a diluted plasma, the respective salts have certain preferable concentrations.

When a human plasma is subjected to a determination by the method of the present invention using, as a standard, a commercially available, freeze-dried control plasma, there occurs discrepancy between the determination results by the method of the present invention and the results obtained by the conventional Thrombin Time Method (see Example 2 to be mentioned later). It is further preferable to select the kind and concentration of the salt, which do not cause such discrepancy.

The concentration of sodium chloride of 1.2–2.0M in the reaction mixture (for example, 2.0–3.0M in reagent) can prevent the discrepancy. However, the coagulation time is shortened in this concentration range, so that sodium bromide is added to prolong the coagulation time, whereby the desirable coagulation time is attained. The similar results can be obtained by adding sodium iodide, potassium bromide, potassium iodide, calcium chloride, magnesium chloride and the like. Preferably, sodium bromide is added to the reaction mixture to a concentration of 0.2–0.7M (e.g. 0.3–1.0M in reagent).

When addition of sodium chloride alone, for example, to a concentration of about 0.25–1.0M in the reaction mixture (ca. 0.5–2.0M in reagent) still results in discrepancy, a discrepancy preventive is added to eliminate the discrepancy. Examples of the discrepancy preventive include salts such as potassium fluoride, sodium fluoride and sodium citrate, and surfactants such as alkyldiaminoethylglycine hydrochloride. The concentration of the discrepancy preventive in the reaction mixture is 0.05–0.2M when potassium fluoride or sodium fluoride is used and 2–50 mM when sodium citrate is used, and the concentration of surfactant is 0.001–0.5 w/v %.

According to Japanese Patent Unexamined Publication No. 219993/1993, the reagent contains 50–250 mM sodium chloride and 2–25 mM calcium chloride. The concentrations of these salts decrease in a reaction mixture and are outside the scope of the present invention.

Japanese Patent Unexamined Publication No. 46898/1994 teaches addition of a salt such as sodium chloride. However, the concentration of the salt is not specified. In this Publication at page 3, Column 4, lines 27–30, it is stated that the ionic strength may be increased by adding a salt such as sodium chloride, and that thrombin was found to be insensitive to AT III inhibition at a low ionic strength. The publication fails to suggest the use of a salt at a high concentration as defined in the present invention. The concentration of sodium chloride is not in the range defined in the present invention, which is 0.5–4M in reagent.

A secondary effect of the present invention is that the need to use a heparin inhibitor such as polybulene is obviated, since the influence of heparin can be mostly avoided at a sodium chloride concentration of not less than 0.6M in a reaction mixture. Advantageously, a preservative such as sodium azide will not be necessary at a high concentration of the salt.

The fibrinogen determination reagent of the present invention contains a salt at a high concentration and 20–500 NIHU/ml thrombin or a protease having a similar activity.

The fibrinogen determination reagent of the present invention consists of one or two kinds of constituent reagents (hereinafter referred to simply as constituents), with preference given to one kind reagent. When a discrepancy preventive is used, the reagent preferably consists of two kinds of constituents, that is, a first reagent containing a discrepancy preventive and a second reagent containing thrombin or a protease having a similar activity. When the reagent of the present invention contains two kinds of constituents, a protease such as thrombin is contained in a second reagent, and a salt is contained in either or both of a first reagent and a second reagent. When the reagent of the present invention contains one kind of constituent, it contains 20–500 NIHU/ml, preferably 40–200 NIHU/ml thrombin, 10–400 mM, preferably 30–200 mM buffer (pH 6.0–9.0, preferably 7.0–8.0) and a salt at a high concentration.

Detailedly speaking, a test sample containing fibrinogen (275 mg/dl) and a reagent containing thrombin (100 NIHU/ml) and HEPES (100 mM, pH 7.35) are mixed at a volume ratio of 1:2, and adjusted to have a salt concentration which produces 5–100 seconds, preferably 7–50 seconds and more preferably 10–30 seconds of coagulation time at 37° C.

Specifically, the salt concentration in the reagent is 0.5–4M, preferably 1.0–3.5M, more preferably 1.5–3M for sodium chloride; 0.15–1.5M for sodium bromide; 0.15–0.6M for sodium iodide; 0.3–2M for potassium chloride; 0.15–1.5M for potassium bromide; 0.15–0.6M for potassium iodide; 0.05–0.35 M for magnesium chloride; and 0.05–0.35M for calcium chloride. While the above-mentioned concentration range may produce 100 seconds or more of a coagulation time by the sole addition of one such salt, a combined use with, for example, sodium chloride affords a coagulation time of not more than 100 seconds.

The aforementioned salts may be used alone or in combination. For achieving a preferable coagulation time in fibrinogen determination, as well as for eliminating discrepancy between the standard and the test sample, two or more salts are preferably used in combination. The combination of two or more salts is not particularly limited, though preferred is the combination of sodium chloride and other salt, more preferably the combination of sodium chloride and sodium bromide.

When two or more salts are used, a test sample containing fibrinogen (275 mg/dl) and a reagent containing thrombin (100 NIHU/ml) and HEPES (100 mM, pH 7.35) are mixed at a volume ratio of 1:2, and adjusted to have a salt concentration which produces 5–100 seconds, preferably 7–50 seconds and more preferably 10–30 seconds coagulation time at 37° C.

The buffer for adjusting pH is not particularly limited and those having a buffer capacity at pH 6.0–9.0, preferably 7.0–8.0 can be used. Examples of such buffer include Tris, phosphate, barbital, imidazole, veronal, glycylglycine, BES, MOPS, TES, HEPES, TAPSO and TAPES buffers, which are commercially available.

In the present invention, various additives can be added on demand for the purpose of maintaining the property and quality of the reagent, production and the like. Examples of the additive include proteins such as BSA, chelating agents such as ethylenediaminetetraacetic acid (EDTA) and ethylene glycol bis(2-aminoethyl ether)-N,N,N',N'-tetraacetic acid (EGTA), antifibrinolysis such as $\epsilon$-aminocaproic acid, tranexamic acid and aprotinine, heparin inhibitors such as polyburene, preservatives such as sodium azide and gentamycin sulfate, surfactants such as polyoxyethylene glycol p-t-octylphenyl ethers (e.g. Triton X-100, trademark) and polyoxyethylene glycol sorbitan alkyl ethers (e.g. Tween 20, trademark), and substances such as sugars (e.g. lactose), amino acids, polyethylene glycol and glycerol.

The fibrinogen determination reagent of the present invention can take the form of a mixture of constituents or an assembly of respective constituents. The mixture of constituents, and respective constituents can be formulated into, by a conventional method, a form permitting direct use for the determination, which is prepared by dissolving the constituents together with excipients in distilled water or buffer to provide a predetermined concentration in the reaction mixture, a form of concentrate to be appropriately diluted to a desired concentration when in use, or a form of a freeze-dry product. Of these, the freeze-dry product is generally employed and the product is dissolved in distilled water or buffer when in use. The respective constituents may take the same form or different forms.

When one kind of constituent is used, the preferred composition of the reagent of the present invention is thrombin 20–500 NIHU/ml, preferably 40–200 NIHU/ml, HEPES 10–400 mM, preferably 30–200 mM, pH 6.0–9.0, preferably pH 7.0–8.0, sodium chloride 0.5–4M, preferably 1.0–3.5M and more preferably 1.5–3M, and sodium bromide 0.15–1.5M, preferably 0.3–1M. As other substances, for example, BSA 0.01–4 w/v % or lactose 0.01–4 w/v % may be contained.

A typical operation of the method of the present invention comprises adding 1–8 fold, preferably 2–3 fold volume of a reagent (total volume when two or more reagents are used) to a test sample (generally plasma) preferably equilibrated at 37° C., and measuring the coagulation time of the reaction mixture by a method known per se. Comparison of the coagulation time with that of the standard results in the determination of fibrinogen in the sample.

The present invention is explained in more detail in the following by way of Examples. In the following Examples, "%" means "w/v %" unless otherwise specified.

EXAMPLE 1

Sodium chloride was added to a solution containing thrombin (100 NIHU/ml, derived from cow, Sigma), 0.5% BSA and 0.1M HEPES (pH 7.35) to a concentration of 0.1–3M. To similar solutions, sodium bromide was added to a concentration of 0.1–3M, potassium chloride to 0.1–1.4M, potassium iodide to 0.1–1.4M, calcium chloride to 0.1–0.4M, and magnesium chloride to 0.1–0.7M, wherein the concentrations are the levels in the reagent.

Figure 1:
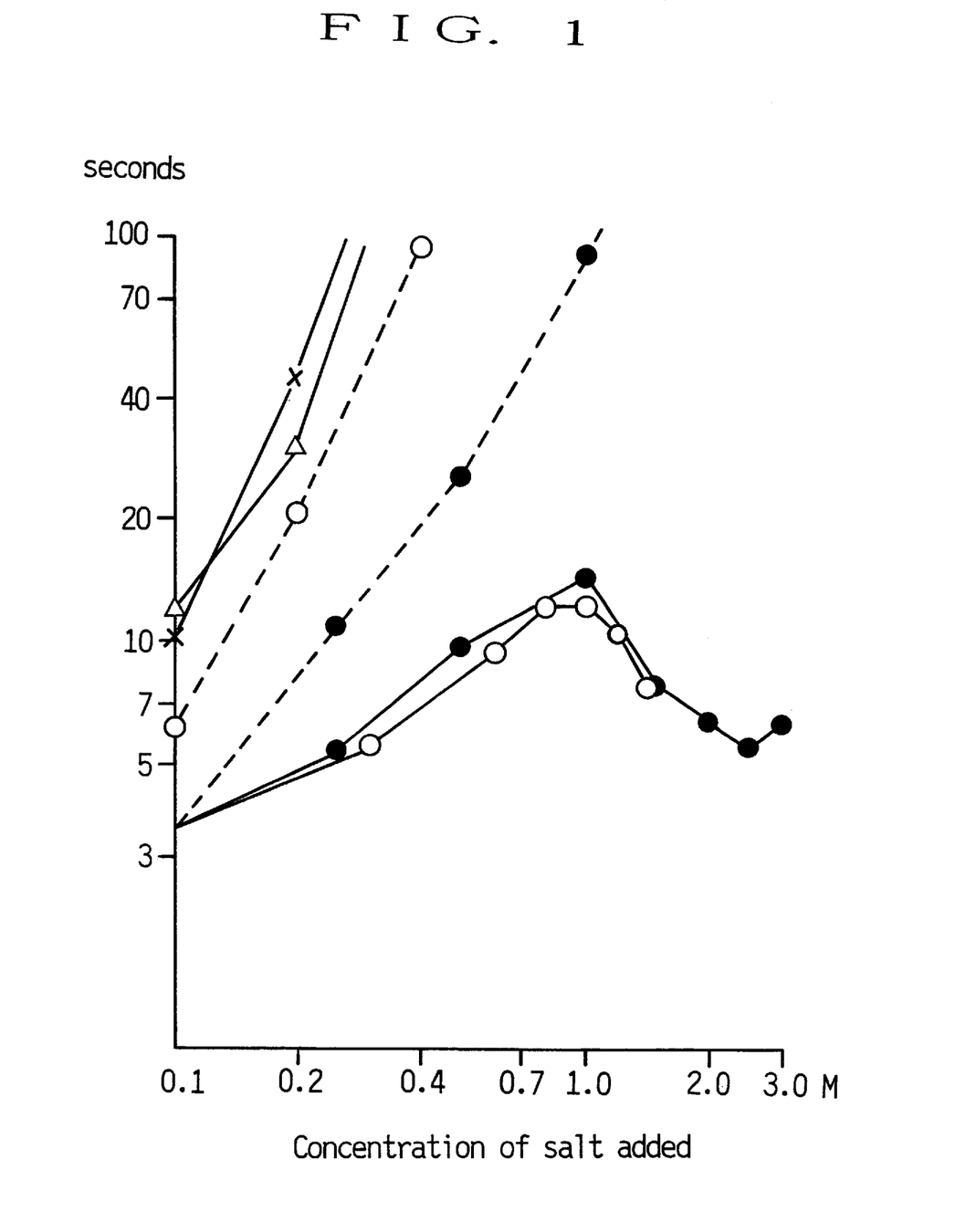
FIG. 1 is a graph showing the relationship between salt concentration and coagulation time, wherein —●— is NaCl, . . . ●. . . is NaBr, —○— is KCl, . . . ○. . . is KI, —X— is $CaCl_2$ and —△— is $MgCl_2$.

An aliquot (100 $\mu$l) from commercially available control plasma Caliplasma (bioMérieux, France) containing 275 mg/dl fibrinogen was heated at 37° C. for 2 minutes. The above-mentioned reagent (200 $\mu$l) placed at room temperature was added, and the coagulation time was measured using a coagulation time measuring equipment KC-4 (Amelung, Germany). The results are shown in FIG. 1.

The coagulation time of 3.5 seconds when using sodium chloride, sodium bromide or potassium chloride at a concentration of 0.1M is the shortest time measurable by a measuring equipment, and the actual coagulation time is considered shorter than this. When sodium chloride was used, the coagulation time became longer with increasing concentrations up to 1M, whereas it was shortened at a concentration of more than 1M. When sodium bromide was used, the coagulation time became longer with increasing concentrations and coagulation did not take place within 300 seconds at 2M. Potassium chloride showed the similar profile to sodium chloride. When potassium iodide was used, the coagulation did not take place within 300 seconds at 0.7M. Magnesium chloride and calcium chloride did not cause coagulation within 300 seconds at 0.4M. It was found that selection of certain concentration for each salt resulted in preferable coagulation time in fibrinogen determination without diluting the test sample.

EXAMPLE 2

To solutions containing thrombin, BSA and HEPES at the same concentrations as in Example 1, sodium chloride was added to a concentration of 1M, sodium bromide to 0.4M, potassium chloride to 0.9M, potassium iodide to 0.2M, calcium chloride to 0.15M, and magnesium chloride to 0.15M, wherein the concentrations are the levels in the reagent.

Commercially available control plasma Caliplasma containing 275 mg/dl fibrinogen or that diluted 1.5-, 2- or 3-fold with physiological saline was used as a test sample. In addition, human plasma samples, regarding which fibrinogen concentration was determined using a commercially available fibrinogen determination reagent kit: Fibrinogen Kit (bioMérieux) according to the conventional Thrombin Time Method, were used as test samples (6 samples). The determination was conducted in the same manner as in Example 1. The results are shown in Table 1.

TABLE 1

Amounts of various salts added and coagulation time of respective samples for fibrinogen determination (unit: seconds, —: not determined)

| fibrinogen | Caliplasma | | | | human plasma test sample | | | | | |
|---|---|---|---|---|---|---|---|---|---|---|
| mg/dl | 275 | 183 | 138 | 92 | 610 | 460 | 380 | 280 | 220 | 160 |
| 1M NaCl | 13.8 | 20.3 | 25.0 | 33.3 | 10.2 | 12.0 | 15.7 | 17.5 | 28.1 | 29.9 |
| 0.4M NaBr | 19.8 | 25.5 | 31.3 | 41.1 | 12.4 | 19.7 | 22.8 | 25.6 | 40.1 | 48.3 |
| 0.9M KCl | 12.5 | 18.9 | 23.0 | 30.7 | 8.5 | 14.1 | 13.9 | 13.9 | 25.8 | 29.0 |
| 0.2M KI | 16.6 | 20.7 | 26.6 | 35.9 | 10.5 | 17.0 | 17.5 | 19.6 | 33.9 | 35.0 |
| 0.15M CaCl$_2$ | 24.1 | 33.1 | 39.4 | 57.4 | 15.4 | — | 20.0 | 25.3 | 37.8 | 40.8 |
| 0.15M MgCl$_2$ | 18.2 | 26.3 | 29.8 | 40.0 | 7.0 | — | 20.2 | 27.0 | 34.6 | 37.8 |

As shown in Table 1, the coagulation time was prolonged by lowering fibrinogen concentration in the presence of the respective salts, when Caliplasma or diluted Caliplasma was used as a test sample. The prolonged coagulation time with lowering fibrinogen concentration was also found in human plasma. This suggests that fibrinogen can be determined using an undiluted test sample. Note that, when commercially available freeze-dried control plasma such as Caliplasma, which is dissolved in water when in use, was used as a standard for fibrinogen determination, the determination values in human plasma, which are obtained based on the standard, become considerably lower than the values obtained according to the conventional dilution method, at the salt concentrations employed in the present Examples. For example, fibrinogen concentration roughly calculated from the coagulation time (seconds) of the sample of human plasma 380 mg/dl in Table 1, based on the value of Caliplasma as a standard, becomes lower by 100 mg/dl or more when sodium chloride is used. This phenomenon can be also found in the case of other salts. Such discrepancy is often disadvantageous, since a commercially available control plasma is frequently used as a standard in actual determinations.

Examples 3 to 5 show preferable conditions which do not cause discrepancy. In Examples 3 and 4, a coagulation time measurement, equipment KC-4, which dynamically detects the formation of aggregates, was used. In Example 5, an equipment for optical determination of the coagulation time was used.

EXAMPLE 3

In this Example, potassium fluoride, sodium citrate and alkyldiaminoethylglycine hydrochloride were used to eliminate the discrepancy in a two reagent system.
Reagent:

A first reagent contained 1M sodium chloride, 0.3M potassium fluoride, 30 mM trisodium citrate, 0.01% alkyldiaminoethylglycine hydrochloride and 0.1M HEPES (pH 7.35). A second reagent contained thrombin 100 NIHU/ml, 0.1M sodium chloride, 0.1% BSA and 0.1M HEPES (pH 7.35).
Determination:

Commercially available control plasma Caliplasma containing 275 mg/dl fibrinogen and that diluted 2-, 3- or 4-fold with physiological saline were used as the standard. The first reagent (100 μl) was added to 100 μl each of the standard and human plasma, and the mixtures were heated at 37° C. for 2 minutes. The second reagent (200 μl) was added and the coagulation time was measured using a coagulation time measurement equipment KC-4 (Amelung, Germany). The fibrinogen in the human plasma was determined from the calibration curve of the standard.

Figure 2:
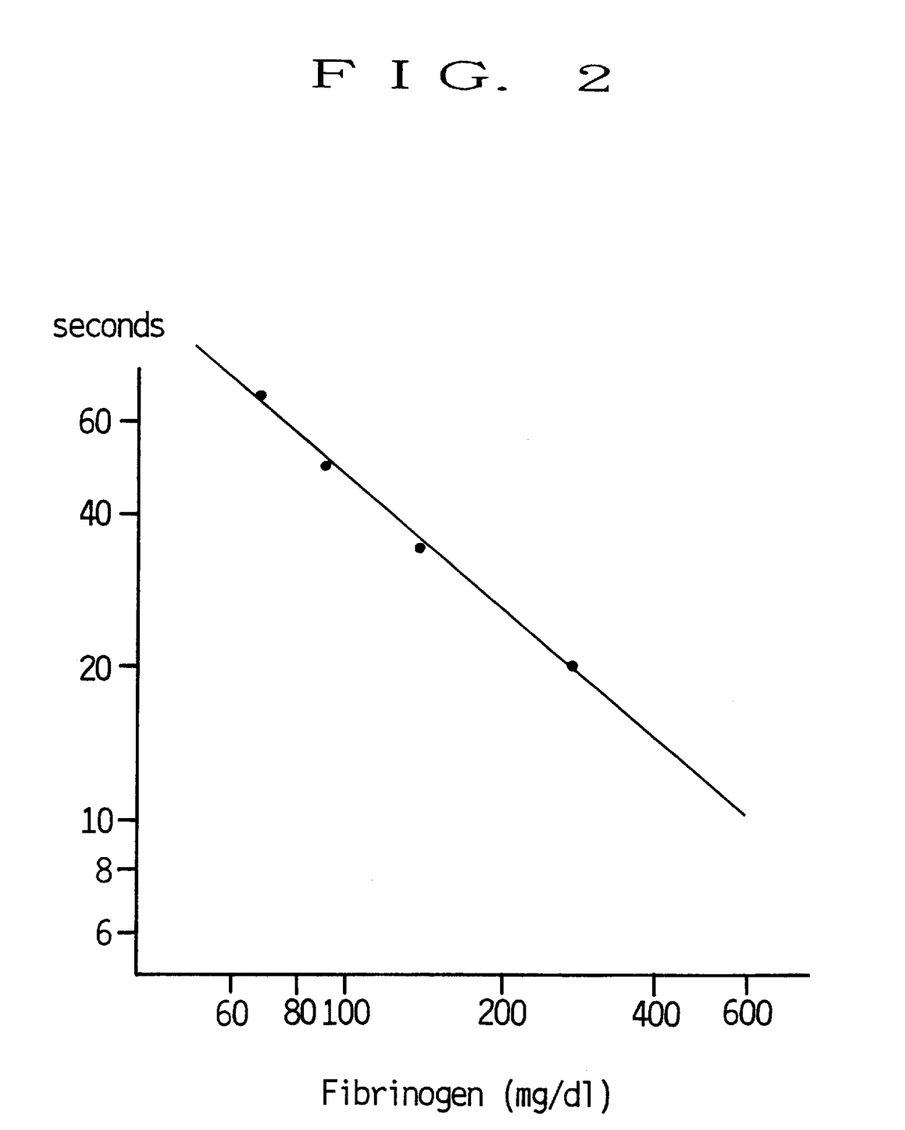
FIG. 2 is a graph showing a calibration curve obtained using a blood coagulation time measuring equipment KC-4 in a two reagent system of the present invention.
Figure 3:
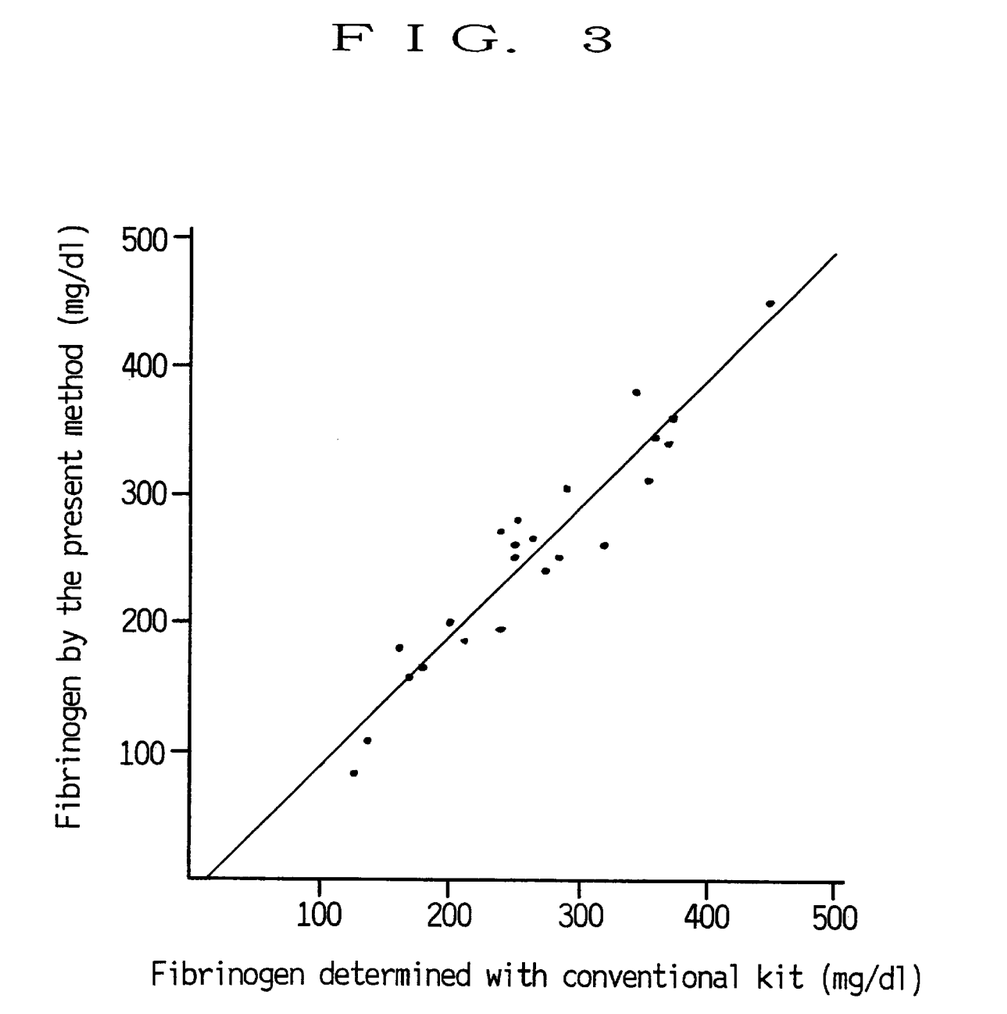
FIG. 3 is a graph showing a correlation with a commercially available kit which was obtained using a blood coagulation time measuring equipment KC-4 in a two reagent system of the present invention, wherein N=23, γ=0.9536, y=1.008x−14, Mean Y=254 and Mean X=266.

In addition, figrinogen in the same commercially available control plasma and human plasma was determined according to the conventional Thrombin Time Method using a commercially available fibrinogen determination reagent kit (Fibrinogen Kit, bioMérieux) and KC-4.
Results:

The calibration curve obtained by the method of the present invention is shown in FIG. 2, wherein a linear relationship between the coagulation time and fibrinogen concentration was obtained on a log-log graph. The coagulation time of the sample containing 250 mg/dl fibrinogen was about 22 seconds. The correlation with the results obtained by the conventional Thrombin Time Method is shown in FIG. 3. A good relationship of correlation coefficient: 0.953 and regression equation: y=1.008x−14 was found in the absence of discrepancy between the results obtained from the human plasma test sample and the results obtained from the standard.

In the following Examples 4 and 5, sodium chloride was used at a high concentration to eliminate the discrepancy between the results obtained from the human plasma test sample and the results obtained from the standard. For prolonging the coagulation time, sodium bromide was added. Note that the discrepancy can be eliminated by the use of sodium chloride at this concentration without using sodium bromide.

EXAMPLE 4

Reagent:
The reagent contained thrombin 100 NIHU/ml, 2.6M sodium chloride, 0.4M sodium bromide, 0.1% BSA and 0.1M HEPES (pH 7.35).
Determination:

Commercially available control plasma Caliplasma containing 275 mg/dl fibrinogen and that diluted 2-, 3-, 4-, 6- or 11-fold with physiological saline were used as the standard. The standard and human plasma (both 100 μl) were heated at 37° C. for 2 minutes and the reagent (200 μl) was added. The coagulation time was measured using a coagulation time measurement equipment KC-4 and the fibrinogen of the human plasma was determined from the calibration curve of the standard.

In addition, fibrinogen in the same commercially available control plasma and human plasma was determined according to the conventional Thrombin Time Method using a commercially available fibrinogen determination reagent kit (Fibrinogen Kit) and KC-4.

Figure 4:
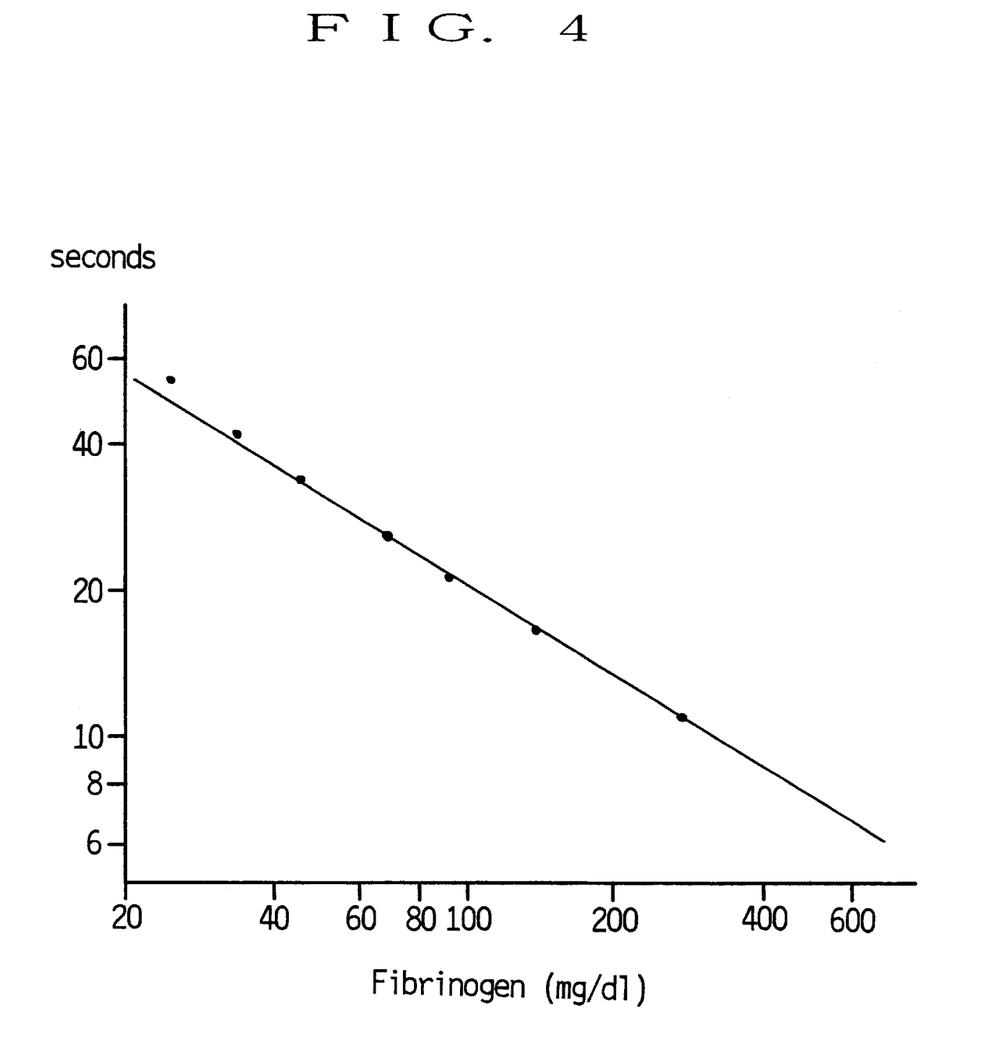
FIG. 4 is a graph showing a calibration curve obtained using a blood coagulation time measuring equipment KC-4 in a one reagent system of the present invention.
Figure 5:
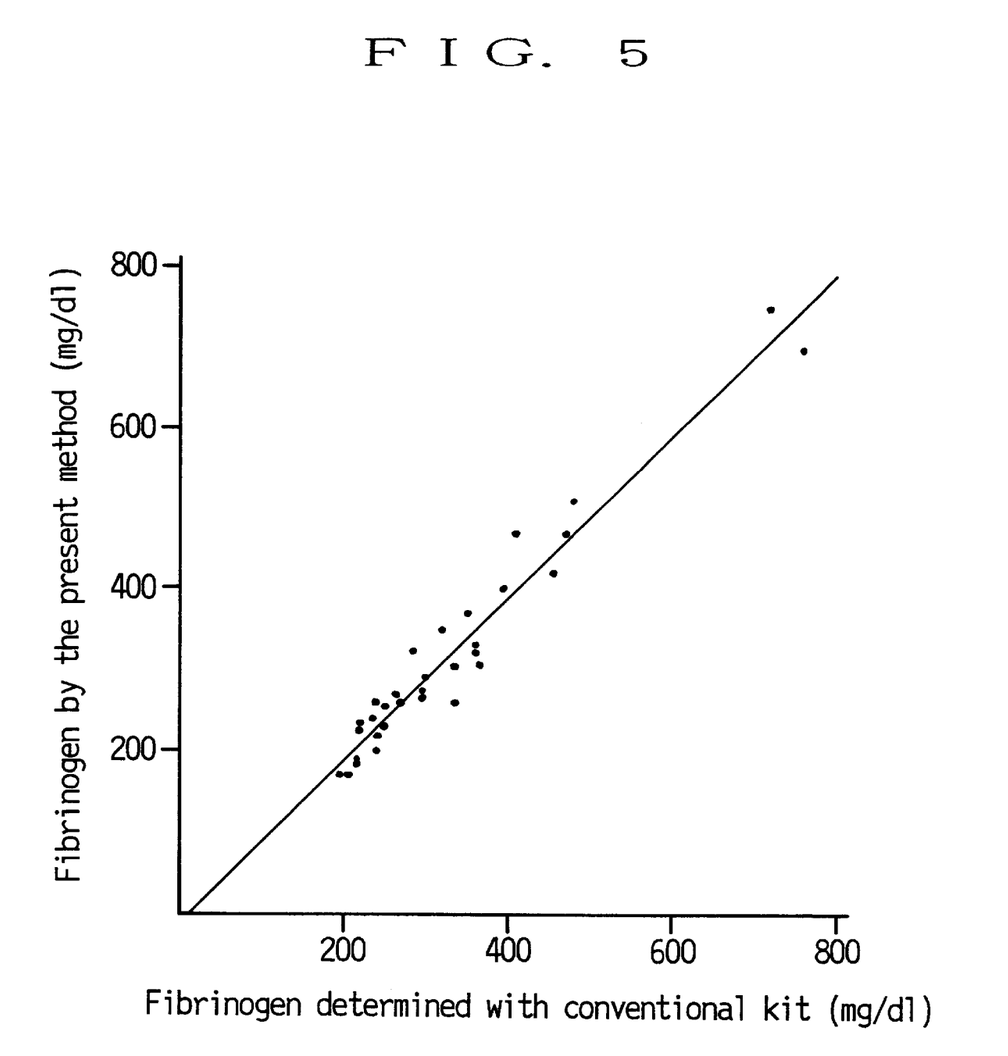
FIG. 5 is a graph showing a correlation with a commercially available kit which was obtained using a blood coagulation time measuring equipment KC-4 in a one reagent system of the present invention, wherein N=36, γ=0.9740, y=1.004x−12, Mean Y=313 and Mean X=323.

Results:

The calibration curve obtained by the method of the present invention is shown in FIG. 4, wherein a linear relationship between the coagulation time and fibrinogen concentration was found on a log-log graph up to the fibrinogen concentration of about 40 mg/dl. The determination was actually possible to the level of 25 mg/dl. The coagulation time of the sample containing 250 mg/dl fibrinogen was about 11.5 seconds. The correlation with the results obtained by the conventional Thrombin Time Method is shown in FIG. 5. A good relationship of correlation coefficient: 0.974 and regression equation: y=1.004x−12 was found in the absence of discrepancy between the results obtained from the human plasma test sample and the results obtained from the standard.

EXAMPLE 5

Reagent:

The reagent contained thrombin 50 NIHU/ml, 2.9M sodium chloride, 0.8M sodium bromide, 0.1% BSA, 0.05% kaolin and 0.1M HEPES (pH 7.35).

Determination:

Commercially available control plasma Caliplasma containing 275 mg/dl fibrinogen and that diluted 2-, 3- or 4-fold with physiological saline were used as the standard. The standard and human plasma (both 100 μl) were heated at 37° C. for 2 minutes and the reagent (200 μl) was added. The coagulation time was measured using a coagulation time measurement equipment Option 8 (bioMérieux) and the fibrinogen of the human plasma was determined from the calibration curve of the standard.

In addition, fibrinogen in the same commercially available control plasma and human plasma was determined according to the conventional Thrombin Time Method using a commercially available fibrinogen determination reagent kit (Fibrinomat Option, bioMérieux) and Option 8.

Figure 6:
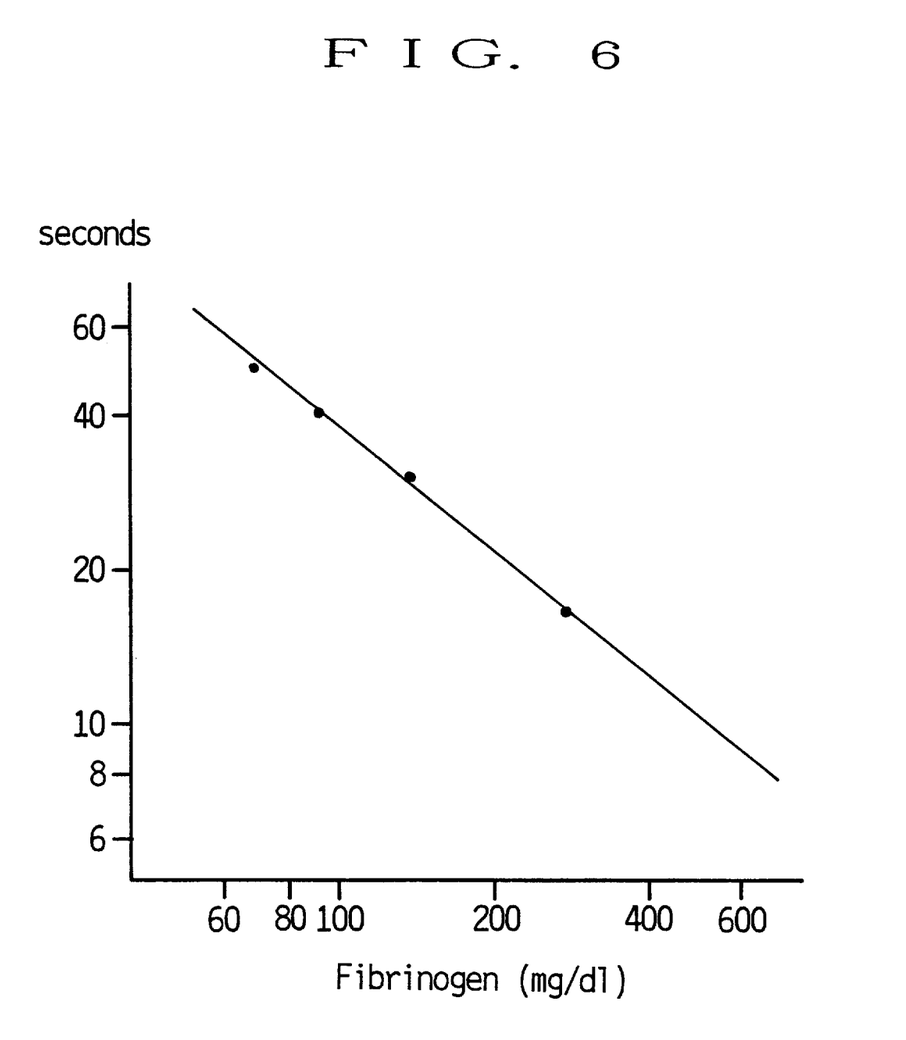
FIG. 6 is a graph showing a calibration curve obtained using a blood coagulation time measuring equipment Option 8 in a one reagent system of the present invention.
Figure 7:
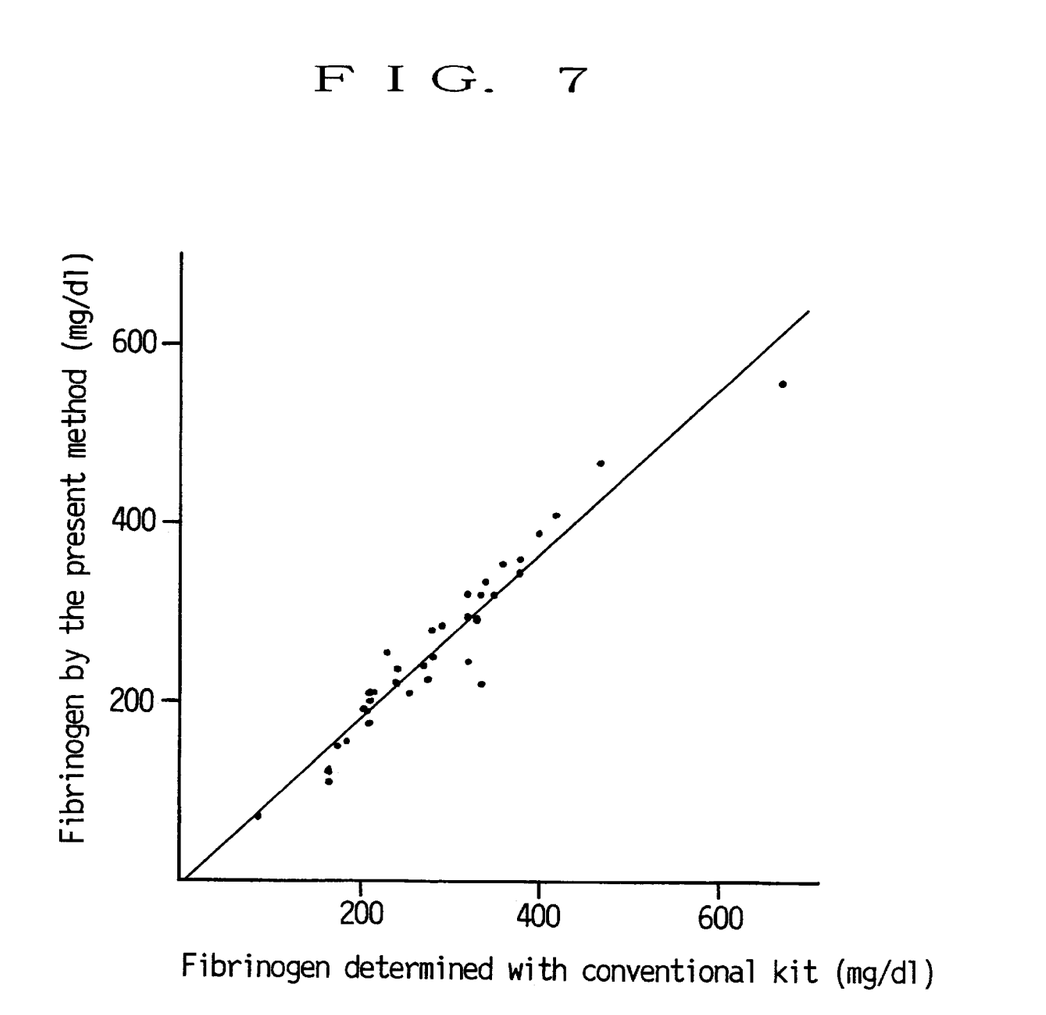
FIG. 7 is a graph showing a correlation with a commercially available kit which was obtained using a blood coagulation time measuring equipment Option 8 in a one reagent system of the present invention, wherein N=36, γ=0.9630, y=0.926x−5, Mean Y=262 and Mean X=289.

Results:

The calibration curve obtained by the method of the present invention is shown in FIG. 6, wherein a linear relationship between the coagulation time and fibrinogen concentration was found on a log-log graph. The coagulation time of the sample containing 250 mg/dl fibrinogen was about 18 seconds. The correlation with the results obtained by the conventional Thrombin Time Method is shown in FIG. 7. A good relationship of correlation coefficient: 0.963 and regression equation: y=0.926x−5 was found. In the instant Example using an equipment optically detecting the coagulation time, discrepancy between the results obtained from the human plasma test sample and the results obtained from the standard was not observed.

A fibrinogen determination according to the Thrombin Time Method but using a salt at a high concentration enables more simplified and easier determination than the conventional diluting method, since the present method does not require diluting of a test sample. The present method is economically advantageous in that a fibrin coagulation inhibitor such as expensive peptide is not used. In addition, the determination is highly precise, since the method adopts the basic principle of the Thrombin Time Method of using an excess amount of thrombin. The method also provides, as secondary effects, a preservative effect and an effect of avoiding the influences of heparin, which are derived from the presence of a salt at a high concentration. The method of the present invention provides the results having a high correlation with the determination results obtained by the conventional dilution method, and can be applied to routine blood coagulation tests.

What is claimed is:

1. A method for determining a fibrinogen concentration, consisting essentially of adding thrombin or a protease having a similar activity thereto to an undiluted test sample to convert fibrinogen in the sample to fibrin, and determining a coagulation time as a measure of fibrinogen concentration, wherein the conversion of the fibrinogen to fibrin is carried out in a solution containing at least one salt selected from the group consisting of sodium salt, potassium salt and magnesium salt at a concentration, said concentration of the salt being set for a level which provides a coagulation time of 5–100 seconds when the coagulation time is measured at 37° C. using a mixture of a sample containing fibrinogen (275 mg/dl), and a reagent containing thrombin (100 NIHU/ml) and HEPES (100 mM, pH 7–35), at a volume ratio of the sample to the reagent of 1:2.

2. The method of claim 1, wherein a sample and a reagent containing thrombin or a protease having a similar activity thereto are mixed at a volume ratio of 1:1–1:8.

3. The method of claim 1, wherein the salt is sodium chloride and the concentration of sodium chloride in the solution is 0.25–3M.

4. The method of claim 1, wherein the salt is sodium chloride and the concentration of sodium chloride in the solution is 0.5–2.5M.

5. The method of claim 1, wherein the salt is sodium chloride and the concentration of sodium chloride in the solution is 1–2M.

6. The method of claim 1, wherein the salt is a mixture of sodium chloride and sodium bromide.

7. The method of claim 1, wherein the the concentration of sodium chloride and sodium bromide is 1–2.5M and 0.1–0.8M, respectively.

8. The method of claim 1, wherein the solution comprises a discrepancy preventive for preventing a discrepancy between the measurements obtained with a test sample and those obtained with a known standard sample.

9. The method of Claim 8, wherein the salt is sodium chloride and the concentration of sodium chloride in the solution is 0.25–1M, and the discrepancy preventive comprises 0.05–0.2M potassium fluoride or sodium fluoride, 2–50 mM sodium citrate and a 0.001–0.5 w/v % surfactant.

10. The method of claim 1, wherein the salt is at least one member selected from the group consisting of sodium chloride, sodium bromide, sodium iodide, potassium chloride, potassium bromide, potassium iodide, and magnesium chloride.

11. The method of claim 10, wherein the concentration of the salt in the solution is 0.25–3M for sodium chloride, 0.1–1.0M for sodium bromide, 0.1–0.4M for sodium iodide, 0.25–1.5M for potassium chloride, 0.1–1M for potassium bromide, 0.1–0.4M for potassium iodide, and 0.04–0.25M for magnesium chloride.

12. The method of Claim 10, wherein sodium chloride is used in combination with another salt.

13. A reagent for determining a fibrinogen quantity consisting essentially of, a salt selected from the group consisting of sodium salt, potassium salt, and magnesium salt, and 20–500 NIHU/ml thrombin or a protease having a similar activity thereto, wherein the concentration of the salt is set for a level which provides a coagulation time of 5–100 seconds when the coagulation time is measured at 37° C. using a mixture of a sample containing fibrinogen (275 mg/dl), and a reagent containing thrombin (100 NIHU/ml) and HEPES (100 mM, pH 7.35) at a volume ratio of the sample and the reagent of 1:2.

14. The reagent of claim 13, wherein the salt is sodium chloride and the concentration of sodium chloride is 0.5–4M.

15. The reagent of claim 13, wherein the salt is sodium chloride and the concentration of sodium chloride is 1–3.5M.

16. The reagent of Claim 13, wherein the salt is sodium chloride and the concentration of sodium chloride is 1.5–3M.

17. The reagent of Claim 13, wherein the salt is a mixture of sodium chloride and sodium bromide.

18. The reagent of Claim 13, wherein the concentration of sodium chloride and sodium bromide is 2–3M and 0.3–1M, respectively.

19. The reagent of Claim 13, wherein the salt is at least one member selected from the group consisting of sodium chloride, sodium bromide, sodium iodide, potassium chloride, potassium bromide, potassium iodide, and magnesium chloride.

20. The reagent of Claim 19, wherein the concentration of the salt in the reagent is 0.5–4M for sodium chloride, 0.15–1.5M for sodium bromide, 0.15–0.6M for sodium iodide, 0.3–2M for potassium chloride, 0.15–1.5M for potassium bromide, 0.15–0.6M for potassium iodide, and 0.05–0.35M for magnesium chloride.

21. The reagent of claim 13, further comprising a discrepancy preventive for preventing a discrepancy between the measurements obtained with a test sample and those obtained with a known standard sample.

22. The reagent of Claim 21, comprising a first reagent comprising the discrepancy preventive, and a second reagent comprising thrombin or a protease having a similar activity thereto, wherein the salt is comprised in either or both of the first reagent and the second reagent.

23. A reagent for determining fibrinogen quantity, consisting essentially of 20–500 NIHU/ml thrombin, 10–400 mM buffer (pH 6.0–9.0), 0.5–4M sodium chloride, and 0.15–1.5M sodium bromide.

24. A reagent for determining fibrinogen quantity, consisting essentially of 40–200 NIHU/ml thrombin, 30–200 mM buffer (pH 7.0–8.0), 1–3.5M sodium chloride, and 0.3–1M sodium bromide.

* * * * *

UNITED STATES PATENT AND TRADEMARK OFFICE
CERTIFICATE OF CORRECTION

PATENT NO. : 5,851,836
DATED : December 22, 1998
INVENTOR(S) : ENOMOTO, Masayasu It is certified that error appears in the above-identified patent and that said Letters Patent is hereby corrected as shown below:

In Table 1, column 9, line 25, second entry in last column under "human plasma test sample": "48.3" should read --46.3--

In Table 1, column 9, line 25, second entry in first column under "Caliplasma": "19.8" should read --19.6--

IN THE CLAIMS:

In claim 1, column 12, line 25: "7-35" should read --7.35--

Signed and Sealed this

Twenty-seventh Day of July, 1999

Attest:

Q. TODD DICKINSON

*Attesting Officer*     *Acting Commissioner of Patents and Trademarks*